United States Patent
Nagatani et al.

(10) Patent No.: US 8,449,829 B2
(45) Date of Patent: May 28, 2013

(54) METHOD OF STERILIZATION IN CLEAN AIR SUPPLY APPARATUS AND CLEAN AIR SUPPLY APPARATUS

(75) Inventors: Nobuaki Nagatani, Tokyo (JP); Takeshi Iwashita, Tokyo (JP)

(73) Assignee: Toyo Seikan Kaisha, Ltd., Tokyo (JP)

( * ) Notice: Subject to any disclaimer, the term of this patent is extended or adjusted under 35 U.S.C. 154(b) by 370 days.

(21) Appl. No.: 12/304,664

(22) PCT Filed: Jun. 27, 2006

(86) PCT No.: PCT/JP2006/313189
§ 371 (c)(1),
(2), (4) Date: Dec. 12, 2008

(87) PCT Pub. No.: WO2008/001471
PCT Pub. Date: Jan. 3, 2008

(65) Prior Publication Data
US 2009/0169421 A1    Jul. 2, 2009

(51) Int. Cl.
*F24F 3/16*    (2006.01)
*A61L 9/015*    (2006.01)

(52) U.S. Cl.
USPC .......................... 422/123; 422/120; 422/124

(58) Field of Classification Search
USPC .......................... 422/120, 123, 124
See application file for complete search history.

(56) References Cited

U.S. PATENT DOCUMENTS

| | | | |
|---|---|---|---|
| 5,879,648 A * | 3/1999 | Hada et al. | 422/304 |
| 6,953,549 B2 * | 10/2005 | Hill et al. | 422/30 |
| 2003/0049165 A1 * | 3/2003 | Yamamoto et al. | 422/28 |

FOREIGN PATENT DOCUMENTS

| | | | |
|---|---|---|---|
| JP | 62-293034 A | | 12/1987 |
| JP | 10-16925 A | | 1/1998 |
| JP | 2001000514 | * | 1/2001 |
| JP | 2005-312799 A | | 11/2005 |

OTHER PUBLICATIONS

English Language Abstract for JP 10-016925; published Jan. 1998.*
English abstract for JP2001000514, published Jan. 2001.*

* cited by examiner

*Primary Examiner* — Sean E Conley
(74) *Attorney, Agent, or Firm* — Lucas & Mercanti, LLP (57) ABSTRACT

A clean air supply apparatus is provided which has an ability of sterilizing effectively and uniformly also a secondary side surface of a filter. The apparatus has a pre-filter 23 for roughly filtering air sequentially introduced from an air inlet port 18 for introducing air to an air supply port 22 for sending clean air to a work environment, a blower 24 for sucking air to the introduced, a heater 25 for adjusting a temperature of introduced air, a chemical agent gas supply apparatus 27, a chemical agent gas eject apparatus 26 for supplying chemical agent gas into the air path, high performance filters or ultrahigh performance filters 41 and 42 for filtering air to be delivered from an air supply port 22 to generate clean air.

6 Claims, 5 Drawing Sheets

METHOD OF STERILIZATION IN CLEAN AIR SUPPLY APPARATUS AND CLEAN AIR SUPPLY APPARATUS

TECHNICAL FIELD

The present invention relates to a sterilizing method of sterilizing an air path including an air path wall, a filter and the like of a clean air supply apparatus for supplying clean air to an work environment covering work apparatuses, and to the clean air supply apparatus.

BACKGROUND ART

In order to remove adverse effects of dust and microbe upon products in a work environment of a food packing factory or the like, a work booth is installed in a clean room or a general room and works are performed by using the inside of the work booth as a work environment, by installing work apparatuses such as a container cleaning apparatus, a content liquid filling apparatus and a capping apparatus.

In order to maintain a clean environment inside a work booth, air is introduced from a clean room or a general room into a clean air supply apparatus, cleaned with a filter and supplied to the work booth. (refer to Patent Documents 1 to 3)

[Patent Document 1] Japanese Patent Laid-open Publication No. 2003-126638

[Patent Document 2] Japanese Patent Laid-open Publication No. Sho-54-162841

[Patent Document 3] Japanese Patent Laid-open Publication No. Sho-51-109143

[Patent Document 4] Japanese Patent Laid-open Publication No. 2005-172285

DISCLOSURE OF THE INVENTION

Problems to be Solved by the Invention

Patent Documents 1 to 3 show clean ail supply technologies for a general industrial clean room. Cleaning technologies adopted by semiconductor factories and the like have been used conventionally in food filling factories without modification. These cleaning technologies are, however, unsatisfactory. Namely, since food itself worked in a food filling factory becomes contamination sources which always release fine particles and microbe, it is necessary to blow always clean air into a work booth. In this context, it becomes necessary to sterilize an apparatus constituting an air path in a clean air supply apparatus, e.g., an air path wall, the surfaces of other apparatuses in the air path, and an output side surface or secondary side surface of a filter. In order to sterilize the secondary side surface of the filter, it can be considered that the secondary side surface is cleaned by blowing chemical agent liquid against the filter secondary side surface from a work environment side. However, installing such a blow cleaning apparatus may become difficult depending upon restrictions of the apparatus structure. Further, since a uniform distribution of chemical liquid blown against the filer may not be obtained, all irregular distribution of sterilizing effects may occur. Furthermore, a performance may be degraded if the filter is wetted with chemical agent. Although Patent Document 4 relates to clean air supply technologies for a food filling apparatus, it does not cite sterilizing technologies for the secondary side surface of a filter. From these reasons, it has been desired to develop air path sterilizing technologies such as sterilizing technologies substituted for blow cleaning, from a work environment side toward a filter secondary side surface.

The present invention has been made in consideration of the above-described circumstances, and has an object of providing a sterilizing method for a clean air supply apparatus having an ability of perfectly and efficiently sterilizing an air path, e.g., filters and a space between the filters, without complicating the structure of a work environment of a food filling factory and the like and without lowering a filter performance, and the clean air supply apparatus.

Means for Solving the Problems

In correspondence with this object, a sterilizing method of the invention for an air path of a clean air supply apparatus for supplying a work environment with clean air, is characterized in that the air path is sterilized by flowing hydrogen peroxide ($H_2O_2$) gas through the air path.

A sterilizing method of the invention for an air path of a clean air supply apparatus for supplying a work environment with clean air, the air path having first and second filters from an upstream portion to a downstream portion, is characterized in that the air path in the downstream portion from a primary side surface of the first filter, including the primary side surface and a secondary side surface of the first filter and primary and secondary side surfaces of the second filter, is sterilized by flowing hydrogen peroxide ($H_2O_2$) gas through the air path.

A clean air supply apparatus of the present invention for supplying clean air to a work environment, is characterized in that the clean air supply apparatus is equipped with a chemical agent gas supply apparatus and also with a pre-filter, a blower, a heater, a chemical agent gas eject apparatus and a filter apparatus sequentially in an air path from all air inlet port to an air supply port, and that the chemical agent gas supply apparatus generates chemical agent gas and supplies the chemical agent gas to the chemical agent gas eject apparatus, the blower sends air into the air path, the heater adjusts a temperature of air in the air path, the chemical agent gas eject apparatus supplies the chemical agent gas into the air path, and the filter apparatus filters air supplied from the air supply to the work environment.

Advantages of the Invention

According to the invention described in claim 1, since the air path of the clean air supply apparatus is sterilized by hydrogen peroxide gas, the uniform sterilizing effects on the air path can be realized without degrading the performance of the filter.

According to the invention described in claim 2, a small consumption amount of hydrogen peroxide can obtain the good sterilizing effects.

According to the invention described in claim 3, a small amount of hydrogen peroxide gas can obtain the better sterilizing effects.

According to the invention described in claim 4, since the air path of the clean air supply apparatus is sterilized by hydrogen peroxide in a gas phase, the uniform sterilizing effects on the air path can be realized without degrading the performance of the filter According to the invention described in claim 5, since sterilizing chemical agent is supplied in the air path of clean air to be sent to the work environment, while the sterilizing chemical agent passes through the air path, it contacts the air path inner wall and filter to sterilize them. Further, since air heated by the heater contacts the filter, the filter secondary side surface is dried, heated and sterilized, the sterilizing function by the sterilizing agent and the sterilizing function by high temperature air are superposed. Since the sterilizing agent reacts the filter secondary side surface in a gas phase, a distribution of chemical agent is uniform so that effective sterilization is possible with a small amount of chemical agent, and moreover, since liquid drops of chemical agent will not attach, the filter performance will not be degraded.

Furthermore, if the filter apparatus is structured by two filters disposed along a flow of chemical agent gas at a predetermined pitch, for example, even if the filter on the work environment side is broken and does not work, the upstream side filter and the air path between two filters are sterilized by chemical agent gas passed through the upstream side filter. There is therefore no fear that contaminated air is supplied to the work environment.

According to the invention described in claim 6, the sterilizing ability of the apparatus can be enhanced by a combination of multiple stages selecting a high performance filter and a ultrahigh performance filter as the two filters.

According to the invention described in claim 7, it is not necessary to mount a nozzle or the like for blowing chemical agent to sterilize the filter secondary side surface from the work environment. The structure of the work environment is not therefore complicated.

According to the invention described in claim 8, it is possible to generate sterilizing chemical agent gas very easily and evaporate the chemical agent efficiently.

According to the invention described in claim 9, since a heated plate is used for evaporating chemical agent, the apparatus structure can be made simple and chemical agent can be evaporated reliably.

According to the invention described in claim 10, since hydrogen peroxide is used as chemical agent, the sterilizing function becomes better.

DESCRIPTION OF REFERENCE NUMERALS

1 . . . filling apparatus, 2 . . . bottle supply apparatus, 3 . . . sterilizing apparatus, 4 . . . rinser, 5 . . . filler, 6 . . . capper, 7 . . . bottle eject apparatus, 8 . . . rinser booth, 11 . . . filler booth, 12 . . . capper booth, 13 . . . clean room or general room, 14 . . . arrow symbol, 16 . . . clean air supply apparatus, 17 . . . air path, 18 . . . air inlet port, 21 . . . air supply port, 29 . . . clean air inlet, 23 . . . pre-filter, 24 . . . blower, 25 . . . heater, 26 . . . chemical agent gas eject apparatus, 27 . . . chemical agent gas supply apparatus, 31 . . . air introducing port, 32 . . . gas outlet port, 33 . . . pre-filter, 34 . . . blower, 35 . . . temperature adjusting member, 36 . . . heating member, 37 . . . air communicating path, 38 . . . heating plate, 41 . . . filter, 42 . . . filter, 51 . . . chemical liquid supply apparatus, 52 . . . drop nozzle, 53 . . . quantitative pump, 54 . . . chemical agent tank

BEST MODE FOR CARRYING OUT THE INVENTION

Description will now be made on the details of the present invention in connection with the accompanying drawings showing one embodiment.

Figure 1:
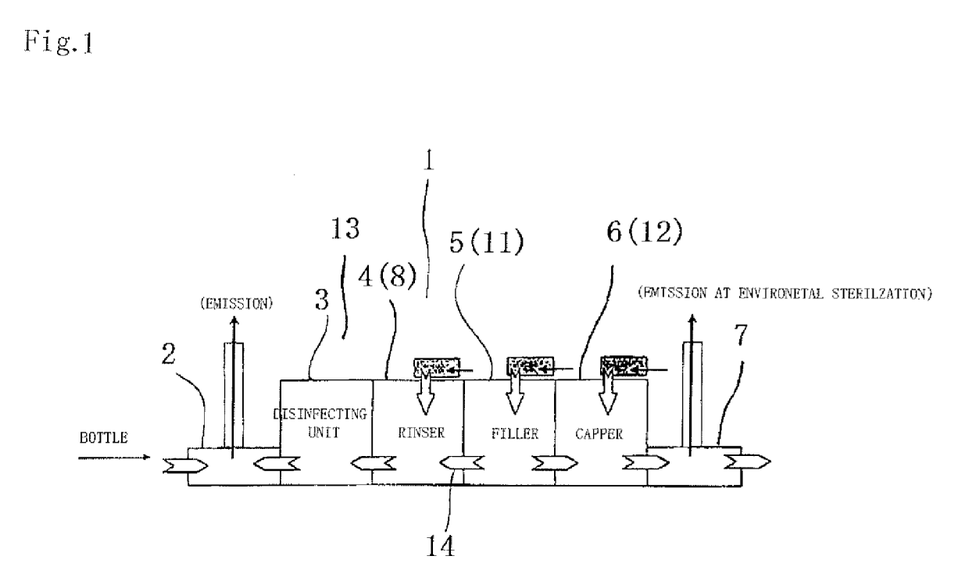
FIG. 1. An illustrative diagram showing the structure of a filling apparatus.

FIG. 1 shows a filler apparatus for drinks. The filler apparatus 1 has a bottle supply apparatus 2, a sterilizing apparatus 3, a rinser 4, a filler 5, a capper 6 and a bottle eject apparatus 7.

A bottle to be filled with a drink enters from the bottle supply apparatus 2 to the filler apparatus 1, is subjected to a sterilizing process at the sterilizing apparatus 3 and to a rinsing process at the rinser 4, is filled with a drink at the filler 5, capped at the capper 6 to complete a filling process, and delivered from the bottle eject apparatus 7.

The work apparatuses of the rinser 4, filler 5 and capper 6 are installed in a rinser booth 8, a filler booth 11 and a capper booth 12, respectively which are work environments enclosed by machine covers, and the rinser booth 8, filler booth 11 and capper booth 12 are installed in a clean room or general room 13. Atmospheric pressures in the rinser booth 8, filler booth 11 and capper booth 12 are maintained at positive pressures. The positive pressures are maintained in such a manner that of these booths, the filler booth 11 installing the filler 5 is highest in pressure, the pressure is lowered toward the terminal booths 8 and 12 and air exhaust is performed as indicated by arrow symbols 14 making the filler booth 11 be set at the most upstream side.

Figure 2:
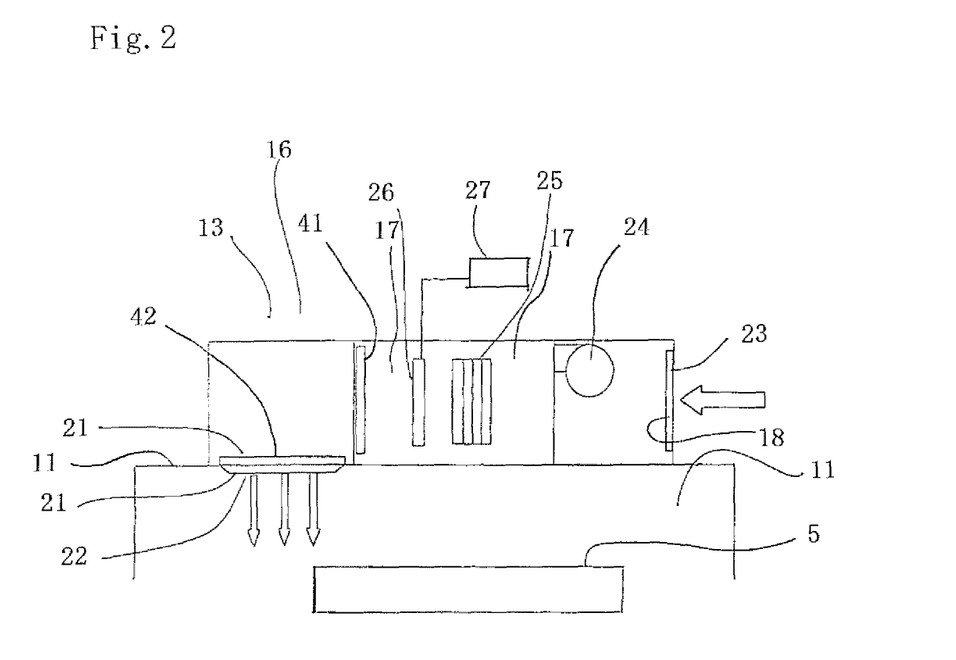
FIG. 2 An illustrative diagram showing the structure of a clean air supply apparatus.

Of the booths 8, 11 and 12, the filler booth 11 of the filler 5 will be described as a representative one. As shown in FIG. 2, the filler booth 11 is equipped with a work apparatus (in this embodiment, filler 5) belongs to which is a clean air supply apparatus 16. The filler 5 is an apparatus for filling a bottle with drink.

The clean air supply apparatus 16 is an apparatus for supplying clean air into the inside of the filler booth 11, and as shown in FIG. 2, has an air path 17 whose air supply port 21 is connected to a clean air inlet 22 of the filler booth 11. A pre-filter 23 is disposed at an air inlet port 18 of the air path 17, a blower 24 is disposed at the downstream side thereof, a heater 25 and a chemical agent gas eject apparatus 26 are disposed at the downstream side thereof, filters 41 and 42 are further disposed at the downstream side thereof. The filter 42 is mounted on the air supply port 21 adjacent to the clean air inlet 22 of the filler booth 11. Each of the filters 41 and 42 is constituted of a high performance filter, a single layer, a plurality of layers of an ultrahigh performance filter, or a combination of a high performance filter and a ultrahigh performance filter. In this embodiment, for example, the filter 41 is constituted of a high performance filter (HEPA) and the filter 42 is constituted of a ultrahigh performance filter (ULPA).

Figure 3:
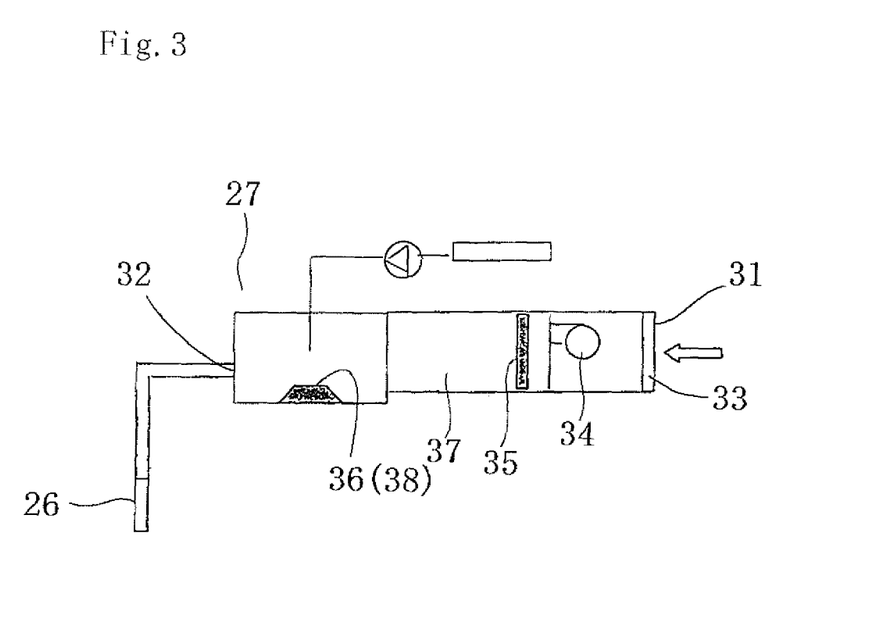
FIG. 3 An illustrative diagram showing the structure of a chemical agent gas supply apparatus.

The pre-filter 23 filters roughly air before entering the air path 17, and removes dusts having a large diameter from the air. The blower 24 is used for introducing air from an external into the clean air supply apparatus 16 and supplies the work environment with clean air. The heater 25 is used for adjusting a temperature or humidity of air moving toward the filters 41 and 42. As shown in FIG. 3, the chemical agent gas supply apparatus 27 is an apparatus for supplying chemical agent in a gas phase to the chemical agent gas eject apparatus 26 such as a nozzle at the air path 17. The chemical agent gas supply apparatus 27 is coupled to the chemical agent gas eject apparatus 26, and has a pre-filter 33, a blower 34, a temperature adjusting member 35 and a heating member 36 in this order front an air introducing port 31 to a gas outlet port 32. The pre-filter 33 is used for filtering roughly air to before being introduced front the air introducing port 31 into an air path communicating path 37, the blower 34 is used for sending air into the air communicating path 37, the temperature adjusting member 35 is used for adjusting a temperature of air in the air communicating path 37, and the heating member 36 is used for heating and evaporating supplied chemical liquid or supplied atomized chemical liquid to generate chemical agent gas. The generated chemical agent gas is sent to the chemical agent gas eject apparatus 26 and supplied to the air path 17. The supplied chemical agent in a gas phase flows through the air path 17 and reaches the filters 41 and 42.

The filters 41 and 42 are disposed at the air supply port 21 of the air path 17. The high performance filter (HEPA) constituting the filter 41 can capture fine particles having a diameter of e.g., not smaller than 0.3 μm at 99.97% or more, to prevent secondary contamination after the high performance filter. The ultrahigh performance filter constituting the filter 42 is a filter for filtering fine particles having a smaller diameter, and can capture fine particles having a diameter of, e.g. not smaller than 0.3 μm at 99.99999% or more. It is preferable that this ultrahigh performance filter is constituted of a water repellent filter given chemical resistance.

In the clean air supply apparatus 16 constructed as above, air in the clean room or general room 13 is supplied to the filler booth 11. Of the air in the clean room or general room 13 introduced by the operation of the blower 24, dusts having a larger diameter are removed by the pre-filter 23, microbe is captured by the filter 41, and microbe and fine particles are removed by the filter 42. A temperature is adjusted with the heater 25 to dry the ultrahigh performance filter 42 and maintain the performance of the ultrahigh performance filter, so that very clean air can be supplied into the filler booth 11.

As chemical agent gas passes through the filter 42, it contacts the secondary side surface to be sterilized. The chemical agent gas entered the filler booth 11 further contacts the secondary side surface of the filter 42 from the filler booth 11 side to be sterilized. Since a distribution of chemical agent in the chemical agent gas is very uniform, even a small amount of chemical agent can sterilize sufficiently effectively the secondary side surface of the filter 42. Further, even if sprays of cleaning agent used for cleaning the inside of the booth are attached to the filter 42, the performance of the filter 42 can be maintained because high temperature chemical agent gas dries the sprays.

Since it is necessary to prevent dew condensation of chemical agent gas in the air path 17, it is necessary that chemical agent gas in the air path 17 is maintained at a temperature not lower than 55° C. at a $H_2O_2$ concentration of, e.g. 1700 to 2400 ppm, or at a temperature not lower than 75° C. at a $H_2O_2$ concentration of 900 to 2400 ppm. A temperature range of chemical agent gas is set within a range not damaging constituent members of the air path.

First Embodiment

Sterilizing effects were verified by using the clean air supply test apparatus of the present invention.

(Test Contents)

Figure 4:
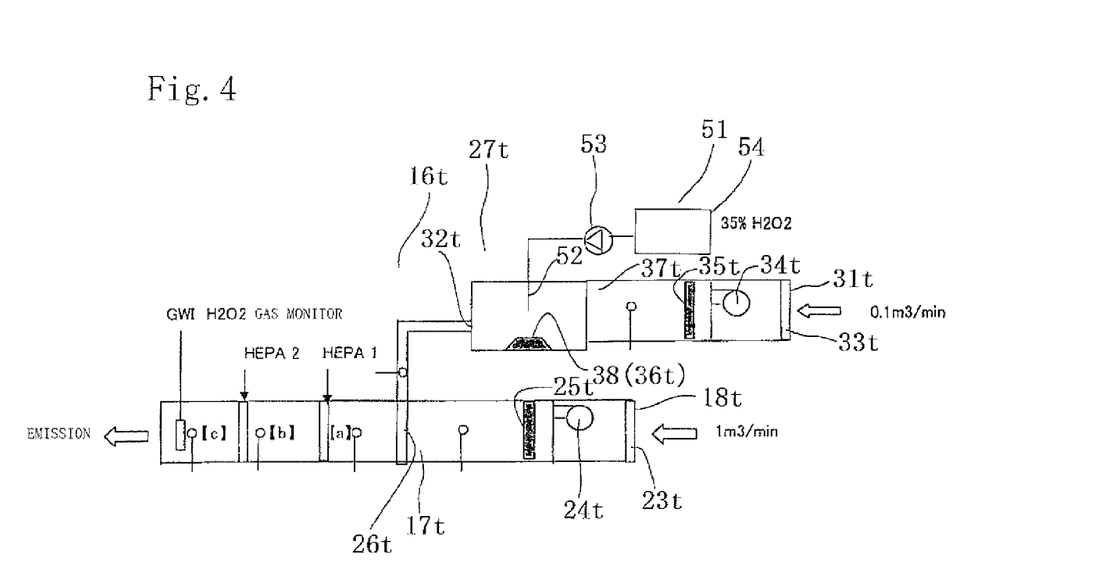
FIG. 4 An illustrative diagram showing the structure of a test apparatus.

The test apparatus is shown in FIG. 4

A test clean air supply apparatus 16t has an air path 17t. A pre-filter 23t is disposed at an air inlet port 18t of the air path 17t, a blower 24t is disposed at the downstream side thereof, a heater 25t and a chemical agent gas eject apparatus 26t for supplying chemical agent gas generated by a chemical agent gas supply apparatus 27t are disposed at the downstream side thereof, and HEPA filters HEPA1 and HEPA2 are further disposed at the downstream side thereof. The chemical agent gas supply apparatus 27t is equipped with a pre-filter 33t, a blower 34t, a temperature adjusting member 35t and a heating member 36t in this order in all air communicating path 37t from an air introducing port 31t to a gas outlet port 32t. The heating member 36t is used for heating and evaporating chemical agent liquid supplied from a chemical liquid supply apparatus 51 to generate chemical agent gas. The chemical liquid supply apparatus 51 for supplying the heating member 36t with chemical agent liquid is equipped with a drop nozzle 52, a quantitative pump 53 and a chemical agent tank 54 to drop chemical agent liquid having a controlled flow rate down to the heating member 36t.

Figure 5:
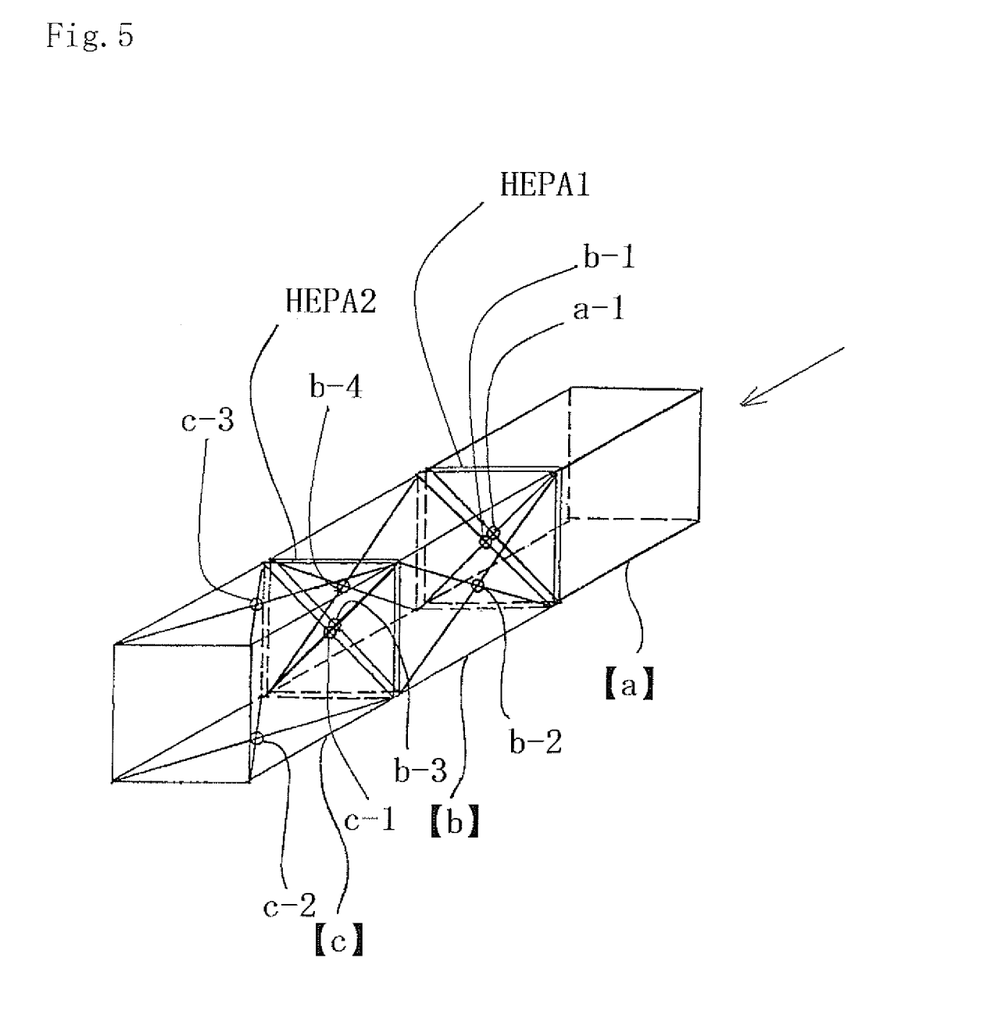
FIG. 5 An illustrative diagram showing the mount positions of indicators of the test apparatus.

(Mount positions of indicators) a1 to a4, b1 to b3, c1 to c3 shown in FIG. 5

(Processes) 1. Filter hot air heating
2. $H_2O_2$ gas heating
(Air flow rate entering from air inlet port 18t) 1 m³/min
(Air flow rate introduced from air introducing port 31t) 0.1 m³/min (Test Method)

Suspended bacteria liquid of *Geobacillus Stearothermophilus* ATCC7953 was attached to an aluminum test piece by $1.8 \times 10^5$ cfu/piece and dried in a clean room.

The formed test piece was adhered to a predetermined position. In a sterilizing process, after a constant temperature was set by using only hot air, 35% $H_2O_2$ was dropped on a hot plate to generate $H_2O_2$ gas to thereby form $H_2O_2$ gas maintained at the temperature. Temp (° C.), $H_2O_2$ gas (ppm), and $H_2O$ gas (ppm) were measured with a $H_2O_2$ gas monitor manufactured by GWI company located in a zone b, and $H_2O_2$ gas was blown for a predetermined time. The test was stopped by stopping generation of $H_2O_2$ and confirming the state not higher than a 0 measurement detection limit of a density meter. Each test piece after sterilization was immersed in an SCD culture medium of 15 ml and cultured for 7 days at 55° C. (+) was added to the culture medium opacified, and (−) was added to the culture medium not opacified.

Test Results

| | | H2O2: 900 ppm H2O: 4700 ppm Temp a: 82° C. b: 79° C. c: 75° C. | | | H2O2: 1700 ppm H2O: 9400 ppm Temp a: 82° C. b: 79° C. c: 75° C. | | | H2O2: 2400 ppm H2O: 12200 ppm Temp a: 82° C. b: 79° C. c: 75° C. | | |
|---|---|---|---|---|---|---|---|---|---|---|
| Zone | Position | 5 min | 10 min | 20 Min | 5 min | 10 min | 20 min | 3 min | 5 min | 10 Min |
| [a] | HEPA11Order a-1 | + | − | − | − | − | − | − | − | − |
| [b] | HEPA12Order b-1 | + | − | − | − | − | − | − | − | − |
| | Wall Front b-2 | + | − | − | + | − | − | − | − | − |
| | HEPA21Order b-3 | + | − | − | − | − | − | − | − | − |
| | Wall Back b-4 | + | + | − | − | − | − | − | − | − |

-continued

| Zone | Position | H2O2: 900 ppm H2O: 4700 ppm Temp a: 82° C. b: 79° C. c: 75° C. | | | H2O2: 1700 ppm H2O: 9400 ppm Temp a: 82° C. b: 79° C. c: 75° C. | | | H2O2: 2400 ppm H2O: 12200 ppm Temp a: 82° C. b: 79° C. c: 75° C. | | |
|---|---|---|---|---|---|---|---|---|---|---|
| | | 5 min | 10 min | 20 Min | 5 min | 10 min | 20 min | 3 min | 5 min | 10 Min |
| [c] | HEPA22Order c-1 | + | − | − | − | − | − | − | − | − |
| | Wall Lower c-2 | + | + | − | − | − | − | − | − | − |
| | Wall Upper c-3 | + | + | − | − | − | − | + | − | − |

| Zone | Position | H2O2: 1700 ppm H2O: 9400 ppm Temp a: 62° C. b: 59° C. c: 55° C. | | | H2O2: 1700 ppm H2O: 9400 ppm Temp a: 82° C. b: 79° C. c: 75° C. | | | H2O2: 1700 ppm H2O: 9400 ppm Temp a: 100° C. b: 98° C. c: 95° C. | | |
|---|---|---|---|---|---|---|---|---|---|---|
| | | 5 min | 10 min | 20 Min | 5 min | 10 min | 20 min | 5 min | 10 min | 20 min |
| [a] | HEPA11Order a-1 | − | − | − | − | − | − | − | − | − |
| [b] | HEPA12Order b-3 | + | − | − | − | − | − | − | − | − |
| | Wall Front b-2 | + | − | − | + | − | − | − | − | − |
| | HEPA21Order b-3 | − | − | − | − | − | − | − | − | − |
| | Wall Back b-4 | − | − | − | − | − | − | − | − | − |
| [c] | HEPA22Order c-1 | − | − | − | − | − | − | − | − | − |
| | Wall Lower c-2 | − | − | − | − | − | − | − | − | − |
| | Wall Upper c-3 | − | − | − | − | − | − | − | − | − |

It has been confirmed from the above test results that sterilization was possible at 55° C., 1700 ppm and 10 min or above, and at 75° C., 900 ppm and 20 min or above.

As described above, according to the present invention, since sterilizing chemical agent is supplied to the air path of clean air to be transported to the work environment, when the sterilizing chemical agent in a gas phase passes through the filter, the secondary side surface is also sterilized. A distribution of chemical components of the gaseous chemical agent is uniform, a small amount of chemical agent can sterilize effectively, and liquid drops of chemical agent will not attach the filter. The performance of the filter will not be therefore degraded.

It is not necessary to mount a nozzle or the like for blowing chemical agent to sterilize the filter secondary side surface from the work environment side so that the structure of the work environment can be simplified.

Industrial Applicability

As apparent from the foregoing description, according to the present invention, it is possible to provide a clean air supplying method and apparatus having an ability of sterilizing effectively an air path, the secondary side surface of a filter, the wall of an air path in the clean air supplying apparatus and the inner surfaces of other apparatuses, without complicating the structure of a work environment of a food filler apparatus.

The invention claimed is:

1. A clean air supply apparatus for supplying clean air to a work environment, wherein the clean air supply apparatus comprises an air inlet, an air supply port, a chemical agent gas supply apparatus, said clean air supply apparatus further comprising a pre-filter, a blower, a heater, a chemical agent gas eject apparatus and a filter apparatus arranged sequentially in an air path from the air inlet to the air supply port, wherein said filter apparatus has at least one filter with a primary side and a secondary side opposing the primary side mounted on the air supply port, adjacent to a clean air inlet of the work environment, wherein said chemical agent gas supply apparatus generates chemical agent gas and supplies the chemical agent gas to the chemical agent gas eject apparatus, said blower sends air into said air path, said heater adjusts a temperature of air in said air path, said chemical agent gas eject apparatus supplies the chemical agent gas into said air path, and said filter apparatus filters air supplied from the air supply port to said work environment, wherein said air path is sterilized by said chemical agent gas supplied to air flowing through said air path to said work environment with said filter being sterilized on said primary side and said secondary side.

2. The clean air supply apparatus according to claim 1, wherein said filter apparatus includes two or more filters disposed at an interval along said air path.

3. The clean air supply apparatus according to claim 1, wherein said chemical agent gas is arranged to contact primary and secondary side surfaces of a filter or filters of said filter apparatus.

4. The clean air supply apparatus according to claim 1, wherein said chemical agent gas supply apparatus is equipped with a pre-filter, a blower, a heater and a heating member sequentially in an air communicating path from an air introducing port to a chemical agent gas delivery port, said pre-filter roughly filters air to be introduced from said air introducing port into said air communicating path, said blower sends air into said air communicating path, said heater adjusts a temperature of air in said air communicating path, and said heating member heats and evaporates supplied chemical agent to generate chemical agent gas.

5. The clean air supply apparatus according to claim 4, wherein said heating member is a heated plate.

6. The clean air supply apparatus according to claim 1, wherein said chemical agent is hydrogen peroxide.

* * * * *